United States Patent
Teuber et al.

(10) Patent No.: US 7,776,900 B2
(45) Date of Patent: Aug. 17, 2010

(54) BENZIMIDAZOLE DERIVATIVES AND THEIR USE FOR MODULATING THE $GABA_A$ RECEPTOR COMPLEX

(75) Inventors: Lene Teuber, Værløse (DK); Janus S. Larsen, Holbæk (DK); Philip K. Ahring, Bagsværd (DK); Elsebet Østergaard Nielsen, København (DK); Naheed Mirza, Birkerød (DK)

(73) Assignee: Neurosearch A/S, Ballerup (DK)

( * ) Notice: Subject to any disclaimer, the term of this patent is extended or adjusted under 35 U.S.C. 154(b) by 383 days.

(21) Appl. No.: 11/918,679

(22) PCT Filed: Apr. 18, 2006

(86) PCT No.: PCT/EP2006/061620

§ 371 (c)(1),
(2), (4) Date: Oct. 17, 2007

(87) PCT Pub. No.: WO2006/111516

PCT Pub. Date: Oct. 26, 2006

(65) Prior Publication Data

US 2009/0030018 A1    Jan. 29, 2009

Related U.S. Application Data

(60) Provisional application No. 60/672,863, filed on Apr. 20, 2005.

(30) Foreign Application Priority Data

Apr. 19, 2005   (DK) ................................ 2005 00567

(51) Int. Cl.
*A61K 31/4184*   (2006.01)
*A61K 31/44*   (2006.01)
*C07D 235/04*   (2006.01)
*C07D 401/02*   (2006.01)

(52) U.S. Cl. .................. 514/394; 548/302.7; 548/304.4; 548/309.7; 548/310.1; 546/268.1; 546/268.4; 546/273.4; 514/336; 514/337; 514/339; 514/385

(58) Field of Classification Search ............. 548/300.1, 548/302.7, 304.4, 306.1, 309.7, 310.1; 546/268.1, 546/268.4, 273.4; 514/336, 337, 339, 385, 514/394

See application file for complete search history.

(56) References Cited

U.S. PATENT DOCUMENTS

| | | | | |
|---|---|---|---|---|
| 6,218,547 B1 * | 4/2001 | Teuber et al. | ............. | 548/304.4 |
| 6,649,609 B2 * | 11/2003 | Teuber et al. | ............. | 514/228.2 |
| 6,710,044 B2 * | 3/2004 | Teuber et al. | ............. | 514/235.8 |
| 6,936,613 B2 * | 8/2005 | Teuber et al. | .......... | 514/252.19 |
| 7,335,777 B2 * | 2/2008 | Teuber et al. | ............. | 548/304.7 |
| 7,419,995 B2 * | 9/2008 | Crew et al. | ................... | 514/394 |
| 7,521,448 B2 * | 4/2009 | Bolger et al. | ............. | 514/234.5 |

FOREIGN PATENT DOCUMENTS

WO    WO-98/34923 A    8/1998
WO    WO-00/78728 A    12/2000

\* cited by examiner

*Primary Examiner*—Golam M Shameem
(74) *Attorney, Agent, or Firm*—Birch, Stewart, Kolasch & Birch, LLP

(57) ABSTRACT

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the $GABA_A$ receptor complex, and in particular for combating anxiety and related diseases.

15 Claims, No Drawings

BENZIMIDAZOLE DERIVATIVES AND THEIR USE FOR MODULATING THE GABA$_A$ RECEPTOR COMPLEX

CROSS REFERENCE TO RELATED APPLICATIONS

This application is the National Phase of PCT/EP2006/061620 filed on Apr. 18, 2006, which claims priority under 35 U.S.C. 119(e) to U.S. Provisional Application No. 60/672,863 filed on Apr. 20, 2005 and under 35 U.S.C. 119(a) to Patent Application No. PA 2005 00567 filed in Denmark on Apr. 19, 2005. Both of these prior applications are hereby expressly incorporated by reference into the present application.

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the targets for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is related to the $\alpha 1$ subunit of the GABA$_A$ receptors. Thus compounds with selectivity for the $\alpha 2$ and/or $\alpha 3$ subunits over the $\alpha 1$ subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of Formula I:

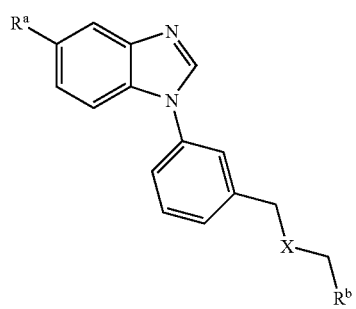

(I)

or an N-oxide thereof, any of its isomers or any mixture of its isomers, or a pharmaceutically acceptable salt thereof, wherein $R^a$, $R^b$ and X are defined as below.

In its second aspect, the invention provides a pharmaceutical composition, comprising a therapeutically effective amount of a compound of the invention, or an N-oxide thereof, any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, or an N-oxide thereof, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of the general formula (I):

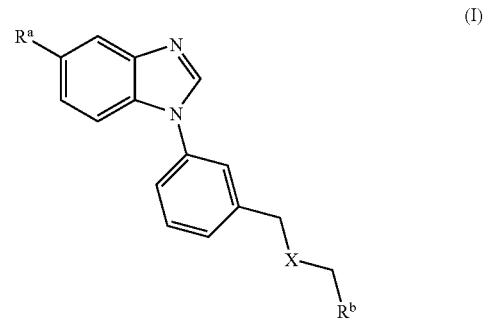

(I)

or an N-oxide thereof, any of its isomers or any mixture of its isomers, or a pharmaceutically acceptable salt thereof, wherein $R^a$ represents halo, trifluoromethyl, trifluoromethoxy, cyano, nitro, $R^c$, $R^cO—$, $R^cO$-alkyl-, $R^c—O—N=(CR^d)—$, $R^c—(C=O)$, $R^c—(C=O)$-akyl-, $R^c—(C=O)—(NR^d)—$, $R^c—(C=O)—(NR^d)$-alkyl-, or $R^c—O—(C=O)—$;

wherein $R^c$ is hydrogen, alkyl, cycloalkyl, cycloalkylakyl, alkenyl, or alkynyl;

which alkyl, cycloalkyl, cycloalkylakyl, alkenyl, and alkynyl is optionally substituted with one or more azido or R'R"N—;

wherein R' and R" independent of each other are hydrogen or alkyl or R' and R" together with the together with the nitrogen to which they are attached form a pyrrolidine or piperidine ring;

$R^d$ is hydrogen or alkyl;

$R^b$ represents an aryl or a heteroaryl group;

which aryl or heteroaryl group is optionally substituted with one or more substituents independently selected from the group consisting of:

halo, hydroxy, R'''R''''N—, R'''R''''N-alkyl, cyano, nitro, trifluoromethyl, trifluoromethoxy, alkoxy, cycloalkoxy, alkyl, cycloalkyl, cycloalkylalkyl, alkenyl, and alkynyl;

wherein R''' and R'''' independent of each other are hydrogen or alkyl; and

X represents —O—, —$NR^e$—;

wherein $R^e$ represents hydrogen or alkyl.

In one embodiment, $R^c$ is hydrogen, alkyl, cycloalkyl, cycloalkylakyl, alkenyl, or alkynyl; which alkyl, cycloalkyl, cycloalkylakyl, alkenyl, and alkynyl is optionally substituted with one or more R'R"N—.

In a second embodiment, $R^a$ represents trifluoromethyl.

In a third embodiment, $R^a$ represents $R^c$ or $R^c$O-alkyl-, wherein $R^c$ represents hydrogen or alkyl. In a special embodiment, $R^a$ represents alkyl, such as methyl. In a further embodiment, $R^a$ represents hydroxyalkyl, such as hydroxymethyl and hydroethyl, e.g. 1-hydroxyethyl. In a still further embodiment, $R^a$ represents alkoxyalkyl, such as alkoxymethyl, such as methoxymethyl. In a further embodiment, $R^a$ represents alkoxyalkyl, such as methoxyethyl and ethoxyethyl, e.g. 1-methoxyethyl, 2-methoxyethyl and 1-ethoxyethyl. In a further embodiment, $R^a$ represents alkyl substituted with azido or R'R"N-alkyl-. In a special embodiment, $R^a$ represents alkyl substituted with azido, such as azidomethyl. In a further embodiment, $R^a$ represents R'R"N-alkyl-. In a special embodiment, R' represents hydrogen and R" represents hydrogen. In a further embodiment, R' and R" together with the together with the nitrogen to which they are attached form pyrrolidin-1-yl. In a still further embodiment, $R^a$ represents aminomethyl or pyrrolidin-1-ylmethyl.

In a still further embodiment, $R^a$ represents $R^c$—O—N=($CR^d$)—, wherein $R^c$ represents hydrogen or alkyl and $R^d$ represents hydrogen or alkyl. In a special embodiment, $R^c$ represents hydrogen. In a further embodiment, $R^c$ represents alkyl, such as ethyl. In a still further embodiment, $R^d$ represents hydrogen. In a further embodiment, R represents alkyl, such as methyl. In a still further embodiment, $R^a$ represents HO—N=(CH)—, HO—N=($CCH_3$)—, $CH_3$O—N=(CH)— or $CH_3CH_2$O—N=($CCH_3$)—.

In a further embodiment, $R^a$ represents $R^c$—(C=O)— or $R^c$—O—(C=O)—, wherein $R^c$ represents hydrogen or alkyl. In a special embodiment, $R^c$ represents alkyl, such as methyl or ethyl. In a still further embodiment, $R^a$ represents methylcarbonyl or ethoxycarbonyl.

In a further embodiment, $R^a$ represents $R^c$—(C=O)—($NR^d$)— or $R^c$—(C=O)—($NR^d$)-alkyl-, wherein $R^c$ represents hydrogen or alkyl and $R^d$ represents hydrogen. In a still further embodiment, $R^a$ represents $R^c$—(C=O)—($NR^d$)—. In a further embodiment, $R^a$ represents $R^c$—(C=O)—($NR^d$)-alkyl-. In a special embodiment, $R^c$ represents alkyl, such as methyl. In a further embodiment, $R^a$ represents acetylaminomethyl.

In a still further embodiment, X represents —O—. In a further embodiment, X represents —$NR^e$—; wherein $R^e$ represents hydrogen or alkyl. In a special embodiment, X represents —NH— or —N($CH_3$)—.

In a further embodiment, $R^b$ represents an optionally substituted aryl group. In a still further embodiment, $R^b$ represents an optionally substituted or a heteroaryl group.

In a still further embodiment, $R^b$ represents an optionally substituted phenyl. In a special embodiment, $R^b$ represents phenyl substituted with one or more halo, such as dihalophenyl, such as dichlorophenyl or difluorophenyl, e.g. 3,4-dichlorophenyl or 3,4-difluorophenyl.

In a further embodiment, $R^b$ represents a heteroaryl group selected from the group of triazolyl, pyridyl, imidazolyl, pyrazolyl, pyrimidyl and thiazolyl; and which heteroaryl group is optionally substituted with one or more substituents as defined above.

In a still further embodiment, $R^b$ represents a heteroaryl group selected from the group of triazolyl, pyridyl, imidazolyl, pyrazolyl, and pyrimidyl; and which heteroaryl group is optionally substituted with one or more alkyl.

In a still further embodiment, $R^b$ represents optionally substituted triazolyl, such as methyltriazolyl or ethyltriazolyl. In a special embodiment, $R^b$ represents 2-methyl-2H-[1,2,4]triazol-3-yl or 2-ethyl-2H-[1,2,4]triazol-3-yl.

In a further embodiment, $R^b$ represents optionally substituted pyridyl, such as pyridyl. In a special embodiment, $R^b$ represents pyridin-2-yl, pyridin-3-yl or pyridin-4-yl.

In a still further embodiment, $R^b$ represents optionally substituted imidazolyl, such as methylimidazolyl. In a special embodiment, $R^b$ represents 1-methyl-1H-imidazol-2-yl.

In a further embodiment, $R^b$ represents optionally substituted pyrazolyl, such as methylpyrazolyl. In a special embodiment, $R^b$ represents 2-methyl-2H-pyrazol-3-yl.

In a further embodiment, $R^b$ represents optionally substituted pyrimidyl, such as pyrimidyl. In a special embodiment, $R^b$ represents pyrimidin-2-yl or pyrimidin-4-yl.

In a further embodiment, $R^b$ represents optionally substituted thiazolyl, such as thiazolyl. In a special embodiment, $R^b$ represents 1,3-thiazol-2-yl.

In a special embodiment the chemical compound of the invention is

1-[3-(Pyridin-2-ylmethoxymethyl)-phenyl]-1H-benzoimidazole-5-carboxylic acid ethyl ester;

1-[3-(1-Methyl-1H-imidazol-2-ylmethoxymethyl)-phenyl]-1H-benzoimidazole-5-carboxylic acid ethyl ester;

1-[3-(2-Methyl-2H-pyrazol-3-ylmethoxymethyl)-phenyl]-1H-benzoimidazole-5-carboxylic acid ethyl ester;

1-[3-(2-Methyl-2H-[1,2,4]triazol-3-ylmethoxymethyl)-phenyl]-1H-benzoimidazole-5-carboxylic acid ethyl ester;

1-[3-(1,3-thiazol-2-ylmethoxymethyl)phenyl]-1H-benzoimidazole-5-carboxylic acid ethyl ester;

1-[3-(Pyridin-3-ylmethoxymethyl)-phenyl]-1H-benzoimidazole-5-carboxylic acid ethyl ester;

1-[3-(Pyrimidin-4-ylmethoxymethyl)-phenyl]-1H-benzoimidazole-5-carboxylic acid ethyl ester;

{1-[3-(Pyridin-2-ylmethoxymethyl)-phenyl]-1H-benzoimidazol-5-yl}-methanol;

{1-[3-(1-Methyl-1H-imidazol-2-ylmethoxymethyl)-phenyl]-1H-benzoimidazol-5-yl}-methanol;

{1-[3-(2-Methyl-2H-[1,2,4]triazol-3-ylmethoxymethyl)-phenyl]-1H-benzoimidazol-5-yl}methanol;

{1-[3-(1,3-Thiazol-2-ylmethoxymethyl)-phenyl]-1H-benzoimidazol-5-yl}-methanol;

{1-[3-(2-Methyl-2H-pyrazol-3-ylmethoxymethyl)-phenyl]-1H-benzoimidazol-5-yl}-methanol (10e);

{1-[3-(Pyridin-3-ylmethoxymethyl)-phenyl]-1H-benzoimidazol-5-yl}-methanol;

{1-[3-(Pyrimidin-4-ylmethoxymethyl)-phenyl]-1H-benzoimidazol-5-yl}-methanol;

5-Methoxymethyl-1-[3-(pyridin-2-ylmethoxymethyl)-phenyl]-1H-benzoimidazole;
5-Methoxymethyl-1-[3-(1-methyl-1H-imidazol-2-ylmethoxymethyl)-phenyl]-1H-benzoimidazole;
5-Methoxymethyl-1-[3-(2-methyl-2H-[1,2,4]triazol-3-ylmethoxymethyl)-phenyl]-1H-benzoimidazole;
5-Methoxymethyl-1-[3-(2-methyl-2H-pyrazol-3-ylmethoxymethyl)-phenyl]-1H-benzoimidazole;
5-Methoxymethyl-1-[3-(1,3-thiazol-2-ylmethoxymethyl)-phenyl]-1H-benzoimidazole;
5-Methoxymethyl-1-[3-(pyridin-3-ylmethoxymethyl)-phenyl]-1H-benzoimidazole;
5-Methoxymethyl-1-[3-(pyrimidin-4-ylmethoxymethyl)-phenyl]-1H-benzoimidazole;
1-[3-(Pyridin-2-ylmethoxymethyl)-phenyl]-5-pyrrolidin-1-ylmethyl-1H-benzoimidazole;
1-[3-(1-Methyl-1H-imidazol-2-ylmethoxymethyl)-phenyl]-5-pyrrolidin-1-ylmethyl-1H-benzoimidazole;
1-[3-(Pyridin-2-ylmethoxymethyl)-phenyl]-1H-benzoimidazole-5-carbaldehyde oxime;
1-[3-(1-Methyl-1H-imidazol-2-ylmethoxymethyl)-phenyl]-1H-benzoimidazole-5-carbaldehyde oxime;
1-[3-(2-Methyl-2H-[1,2,4]triazol-3-ylmethoxymethyl)-phenyl]-1H-benzoimidazole-5-carbaldehyde oxime;
O-Methyl 1-[3-(2-methyl-2H-[1,2,4]triazol-3-ylmethoxymethyl)-phenyl]-1H-benzoimidazole-5-carbaldehyde oxime;
1-[3-(2-Methyl-2H-pyrazol-3-ylmethoxymethyl)-phenyl]-1H-benzoimidazole-5-carbaldehyde oxime;
O-Methyl 1-[3-(2-methyl-2H-pyrazol-3-ylmethoxymethyl)-phenyl]-1H-benzoimidazole-5-carbaldehyde oxime;
1-[3-(1,3-Thiazol-2-ylmethoxymethyl)-phenyl]-1H-benzoimidazole-5-carbaldehyde oxime;
O-Methyl 1-[3-(1,3-thiazol-2-ylmethoxymethyl)-phenyl]-1H-benzoimidazole-5-carbaldehyde oxime;
1-[3-(Pyridin-3-ylmethoxymethyl)-phenyl]-1H-benzoimidazole-5-carbaldehyde oxime;
1-[3-(Pyrimidin-4-ylmethoxymethyl)-phenyl]-1H-benzoimidazole-5-carbaldehyde oxime;
C-{1-[3-(1-Methyl-1H-imidazol-2-ylmethoxymethyl}-phenyl]-1H-benzoimidazol-5-yl) methylamine;
C-{1-[3-(Pyridin-2-ylmethoxymethyl)-phenyl]-1H-benzoimidazol-5-yl}-methylamine;
N-{1-[3-(1-Methyl-1H-imidazol-2-ylmethoxymethyl)-phenyl]-1H-benzoimidazol-5-ylmethyl}-acetamide;
N-{1-[3-(Pyridin-2-ylmethoxymethyl)-phenyl]-1H-benzoimidazol-5-ylmethyl}-acetamide;
N-{1-[3-(2-Methyl-2H-[1,2,4]triazol-3-ylmethoxymethyl)-phenyl]-1H-benzoimidazol-5-ylmethyl}-acetamide;
N-{1-[3-(2-Methyl-2H-pyrazol-3-ylmethoxymethyl)-phenyl]-1H-benzoimidazole-5-ylmethyl}-acetamide;
N-{1-[3-(1,3-Thiazol-2-ylmethoxymethyl)-phenyl]-1H-benzoimidazole-5-ylmethyl}-acetamide;
1-[3-(2-Methyl-2H-[1,2,4]triazol-3-ylmethoxymethyl)-phenyl]-5-trifluoromethyl-1H-benzoimidazole;
1-[3-(2-Ethyl-2H-[1,2,4]triazol-3-ylmethoxymethyl)-phenyl]-5-trifluoromethyl-1H-benzoimidazole;
5-Methyl-1-[3-(2-methyl-2H-[1,2,4]triazol-3-ylmethoxymethyl)-phenyl]-1H-benzoimidazole;
1-{1-[3-(2-Methyl-2H-[1,2,4]triazol-3-ylmethoxymethyl)-phenyl]-1H-benzoimidazol-5-yl}-ethanone;
1-{1-[3-(2-Methyl-2H-[1,2,4]triazol-3-ylmethoxymethyl)-phenyl]-1H-benzoimidazol-5-yl}-ethanone oxime;
1-{1-[3-(2-Methyl-2H-[1,2,4]triazol-3-ylmethoxymethyl)-phenyl]-1H-benzoimidazol-5-yl}-ethanone O-ethyl-oxime;
1-{1-[3-(2-Methyl-2H-[1,2,4]triazol-3-ylmethoxymethyl)-phenyl]-1H-benzoimidazol-5-yl}-ethanone O-methyl-oxime;
1-{1-[3-(2-Methyl-2H-[1,2,4]triazol-3-ylmethoxymethyl)-phenyl]-1H-benzoimidazol-5-yl}-ethanol;
5-(1-Methoxy-ethyl)-1-[3-(2-methyl-2H-[1,2,4]triazol-3-ylmethoxymethyl)-phenyl]-1H-benzoimidazole;
5-(1-Ethoxy-ethyl)-1-[3-(2-methyl-2H-[1,2,4]triazol-3-ylmethoxymethyl)-phenyl]-1H-benzoimidazole;
5-Azidomethyl-1-[3-(thiazol-2-ylmethoxymethyl)-phenyl]-1H-benzoimidazole;
5-Azidomethyl-1-[3-(2-methyl-2H-[1,2,4]triazol-3-ylmethoxymethyl)-phenyl]-1H-benzoimidazole;
5-Azidomethyl-1-[3-(2-Methyl-2H-pyrazol-3-ylmethoxymethyl)-phenyl]-1H-benzoimidazole;
C-{1-[3-(1,3-Thiazol-2-ylmethoxymethyl)-phenyl]-1H-benzoimidazole-5-yl}-methylamine;
C-{1-[3-(2-Methyl-2H-[1,2,4]triazol-3-ylmethoxymethyl)-phenyl]-1H-benzoimidazol-5-yl}-methylamine;
C-{1-[3-(2-Methyl-2H-pyrazol-3-ylmethoxymethyl)-phenyl]-1H-benzoimidazol-5-yl}-methylamine;
1-{3-[(3,4-Difluoro-benzylamino)-methyl]-phenyl}-1H-benzoimidazole-5-carboxylic acid ethyl ester;
1-(3-{[(Pyridin-2-ylmethyl)-amino]-methyl}phenyl)-1H-benzoimidazole-5-carboxylic acid ethyl ester;
1-(3-{[(Pyridin-4-ylmethyl)-amino]-methyl}-phenyl)-1H-benzoimidazole-5-carboxylic acid ethyl ester;
1-(3-{[(Pyridin-3-ylmethyl)-amino]-methyl}-phenyl)-1H-benzoimidazole-5-carboxylic acid ethyl ester;
1-{3-[(3,4-Dichloro-benzylamino)-methyl]-phenyl}-1H-benzoimidazole-5-carboxylic acid ethyl ester;
(1-{3-[(3,4-Difluoro-benzylamino)-methyl]-phenyl}-1H-benzoimidazol-5-yl)-methanol;
(3,4-Difluoro-benzyl)-[3-(5-methoxymethyl-benzoimidazol-1-yl)-benzyl]-methyl-amine;
1-{3-[(3,4-Difluoro-benzylamino)-methyl]-phenyl}-1H-benzoimidazole-5-carbaldehyde;
1-{3-[(3,4-Difluoro-benzylamino)-methyl]-phenyl}-1H-benzoimidazole-5-carbaldehyde oxime;

or an N-oxide thereof, any of its isomers or any mixture of its isomers, or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention an aryl group designates a carbocyclic aromatic ring system such as phenyl, naphthyl (1-naphthyl or 2-naphthyl) or fluorenyl.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, 1,2,4-oxadiazolyl, 1,2,4-thiadiazolyl, 1,2,5-oxadiazolyl, 1,2,5-thiadiazolyl, triazolyl, imidazolyl, pyrrolyl, pyrazolyl, furanyl, thienyl, pyridyl, pyrimidyl, pyridazinyl or pyrazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-Oxides

In the context of this invention an N-oxide designates an oxide derivative of a nitrogen containing compound, e.g. N-containing heterocyclic compounds capable of forming such N-oxides, and compounds holding one or more amino groups. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease;

cerebral ischemia, stroke, head trauma;

tinnitus: and disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 μM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: All reactions involving air sensitive reagents or intermediates were performed under nitrogen and in anhydrous solvents. Magnesium sulphate or sodium sulphate was used as drying agent in the workup-procedures and solvents were evaporated under reduced pressure.

Example 1

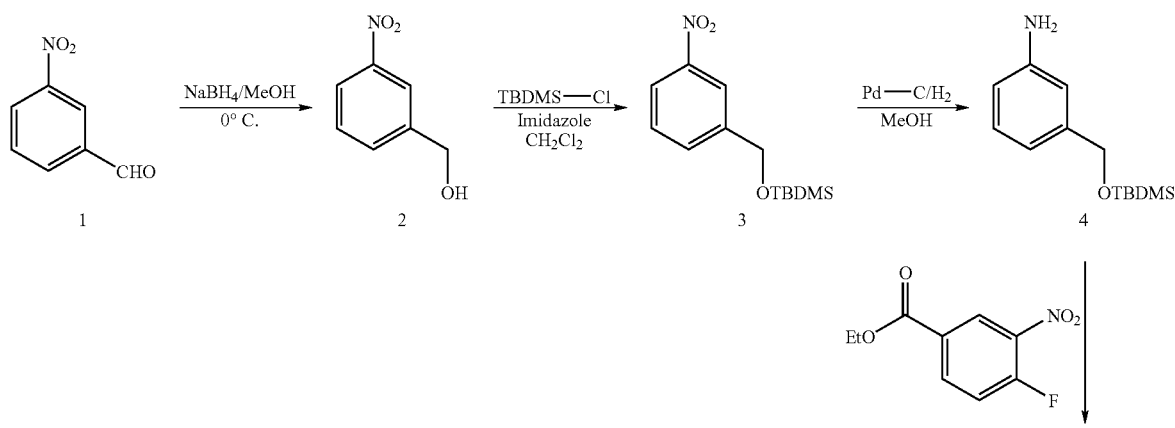

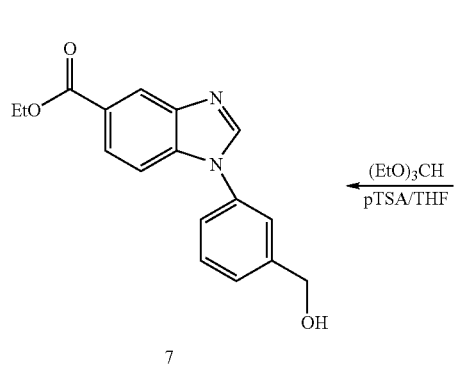
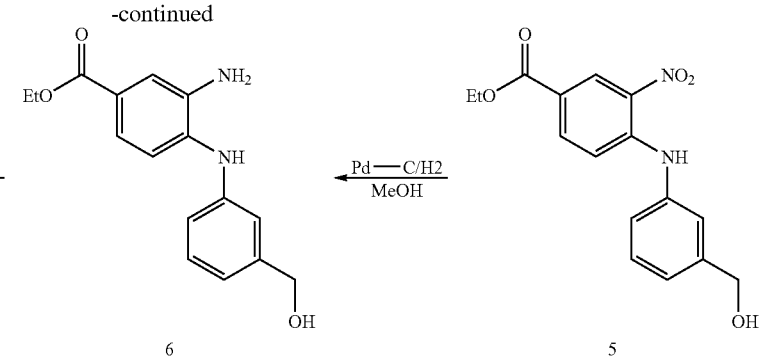

Procedure for Synthesis of Compound 2

To a solution of 3-nitrobenzaldehyde (1) (200 g, 1.32 mol) in methanol (1000 mL) at 0° C. under $N_2$ was slowly added $NaBH_4$ (25 g, 0.66 mol) and the reaction mixture was stirred at RT for 1 hour. The reaction mixture was again cooled to 0° C. and quenched with ice-water. Methanol was removed under reduced pressure and the residue was extracted with $CH_2Cl_2$ (5×200 mL). The combined organic layers were washed with brine, dried over anhydrous $Na_2SO_4$ and evaporated to afford compound 2 (190.7 g, 93.7%) as a liquid, which was taken as such for the next step.

Procedure for Synthesis of Compound 3

To a solution of compound 2 (4.7 g, 0.03 mol) and imidazole (2.71 g, 0.04 mol) in dry $CH_2Cl_2$ (30 mL) in a $N_2$ atmosphere at 0° C. was added a solution of TBDMS-Cl (5.08 g, 0.033 mol) in $CH_2Cl_2$ (15 ml). Then the reaction mixture was stirred at RT for 3 hours. The precipitated solid was filtered off and washed with $CH_2Cl_2$. The filtrate and the combined $CH_2Cl_2$ washings were dried over anhydrous $Na_2SO_4$, the solvent was removed under reduced pressure and the residue was purified by column chromatography on silica gel using a 3:7 mixture of ethyl acetate and pet-ether as the eluent to afford compound 3 (7.2 g, 87%) as a liquid.

Procedure for Synthesis of Compound 4

A solution of compound 3 (7.2 g, 0.027 mol) in dry methanol was hydrogenated to completion using Pd—C (0.72 g) as catalyst (the reaction was monitored by TLC). Then the reaction mixture was filtered through celite, the filter cake was washed with methanol and the combined organic solvent was concentrated under reduced pressure to afford compound 4 (5.0 g, 94%) as a liquid which was taken as such for the next step.

4-(3-Hydroxymethyl-phenylamino)-3-nitro-benzoic acid ethyl ester (5)

A mixture of compound 4 (1.0 g, 4.2 mmol), ethyl 4-fluoro-3-nitro benzoate (0.89 g, 4.2 mmol), N-methyl-2-pyrrolidone (NMP) (4 mL) and N-ethyl isopropyl amine (0.65 g, 5 mmol) was stirred at 80° C. for 3 hours. The cooled reaction mixture was diluted with water (20 mL) and the product was extracted with ethyl acetate (3×40 mL). The combined organic layers were washed with brine, dried over anhydrous $Na_2SO_4$ and concentrated under reduced pressure. This concentrate was purified by column chromatography on silica gel using a 4:6 mixture of ethyl acetate and pet-ether as the eluent to afford compound 5 (0.8 g, 60%) as a solid.

3-Amino-4-(3-hydroxymethyl-phenylamino)-benzoic acid ethyl ester (6)

A solution of compound 5 (10 g, 30 mmol) in dry methanol (80 mL) was hydrogenated using Pd—C (1.0 g) as the catalyst (reaction monitored by TLC). The reaction mixture was filtered through celite. The filter cake was washed with methanol and the combined filtrate and washings were concentrated under reduced pressure to afford compound 6 (8.5 g, 93%) as a solid, which was taken as such for the next step.

1-(3-Hydroxymethyl-phenyl)-1H-benzoimidazole-5-carboxylic acid ethyl ester (7)

A solution of compound 6 (8.5 g), triethylorthoformate (7.55 mL), p-toluene sulphonic acid (2 g) in THF (75 mL) was stirred at reflux for 4 hours. The reaction mixture was concentrated under reduced pressure. The residue was dissolved in $CH_2Cl_2$ (600 mL), washed with 20% $NaHCO_3$ solution and brine, successively, and dried over anhydrous $Na_2SO_4$. The solvent was removed under reduced pressure and the crude product was purified by column chromatography on silica gel using a 4:6 mixture of ethyl acetate and pet-ether as the eluent to afford compound 7 (7.9 g, 77%) as a solid.

Example 2

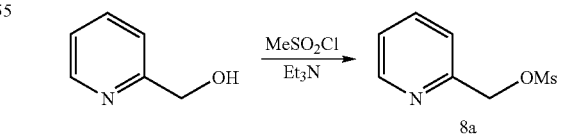

Procedure for Synthesis of Compound 8a

To an ice cold solution of 2-pyridylcarbinol (330 mg, 3.0 mmol) and triethyl amine (0.92 ml) in dry THF (10 mL) was added a solution of mesylchloride (0.23 mL) in dry THF (2 mL). The reaction mixture was stirred for 3 hours at 0° C. The reaction mixture was concentrated under reduced pressure and the residue was dissolved in $CH_2Cl_2$ (100 mL), washed with brine and dried over anhydrous $Na_2SO_4$. The solvent was removed under reduced pressure to afford compound 8a (560 mg, 97%).

In analogy herewith, the following compounds were prepared:

Methanesulphonic acid 1-methyl-1H-imidazol-2-ylmethyl ester (8b)

Methanesulphonic acid 2-methyl-2H-[1,2,4]triazol-3-ylmethyl ester (8c)

Methanesulphonic acid 2-methyl-2H-pyrazol-3-ylmethyl ester (8e)

Methanesulphonic acid 1,3-thiazol-2-ylmethyl ester (8g)

as are:

Methanesulphonic acid pyridin-3-ylmethyl ester (8d) and

Methanesulphonic acid pyrimidin-4-ylmethyl ester (8f)

Example 3

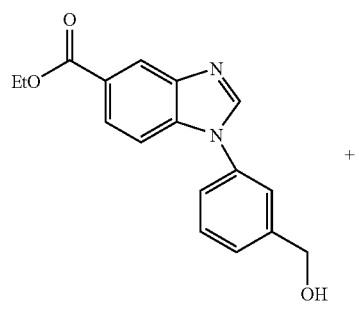
7

+

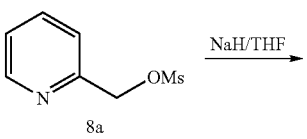
8a

NaH/THF ⟶

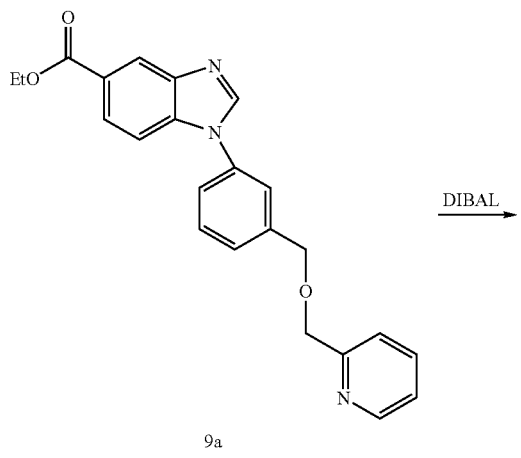
9a

DIBAL ⟶

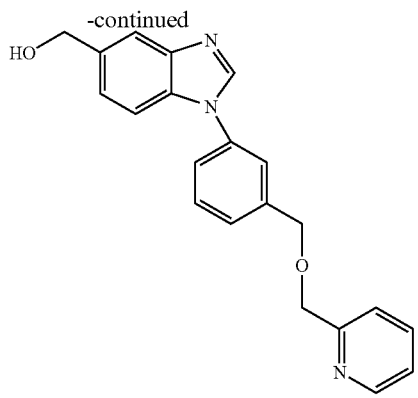
10a

NaH/THF
CH₃I ↓

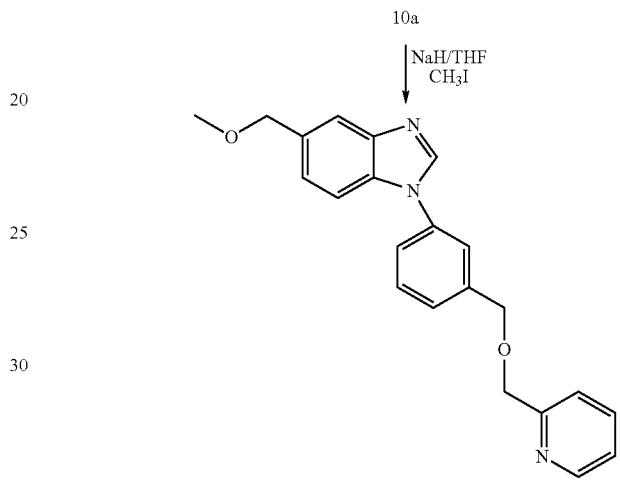
11a

1-[3-(Pyridin-2-ylmethoxymethyl)-phenyl]-1H-benzoimidazole-5-carboxylic acid ethyl ester (9a)

To a suspension of NaH (180 mg) in dry THF (5 mL) at 0° C. in a $N_2$ atmosphere was added a solution of compound 7 (800 mg, 3 mmol) in dry THF (5 mL) and the reaction mixture was stirred for 30 min at 0° C. Then compound 8a (560 mg, 3 mmol) was added and stirring was continued for 12 hours at RT. The reaction mixture was quenched with water, concentrated under reduced pressure to remove THF and extracted with $CH_2Cl_2$ (100 mL). The extract was washed with brine, dried over anhydrous $Na_2SO_4$ and evaporated under reduced pressure. The crude product was purified by column chromatography on silica gel using a 4:6 mixture of ethyl acetate and pet-ether as the eluent to afford compound 9a (300 mg) as a solid, Mp 99.8-101.2° C.

In analogy herewith, the following compounds were prepared:

1-[3-(1-Methyl-1H-imidazol-2-ylmethoxymethyl)-phenyl]-1H-benzoimidazole-5-carboxylic acid ethyl ester (9b) from 8b. Mp 126-129° C.

1-[3-(2-Methyl-2H-pyrazol-3-ylmethoxymethyl)-phenyl]-1H-benzoimidazole-5-carboxylic acid ethyl ester (9e) from 8e. LC-ESI-HRMS of [M+H]+ shows 391.1767 Da. Calc. 391.177025 Da, dev. −0.8 ppm 1-[3-(2-Methyl-2H-[1,2,4]triazol-3-ylmethoxymethyl)-phenyl]-1H-benzoimidazole-5-carboxylic acid ethyl ester (9c) from 8c. LC-ESI-HRMS of [M+H]+ shows 392.1731 Da. Calc. 392.172225 Da, dev. 2.2 ppm 1-[3-(1,3-thiazol-2-ylmethoxymethyl)phenyl]-1H-benzoimidazole-5-carboxylic acid ethyl ester (9g) from 8g. Mp. 76-78° C., and likewise prepared are:

1-[3-(Pyridin-3-ylmethoxymethyl)-phenyl]-1H-benzoimidazole-5-carboxylic acid ethyl ester (9d) from 8d 1-[3-(Pyrimidin-4-ylmethoxymethyl)-phenyl]-1H-benzoimidazole-5-carboxylic acid ethyl ester (9f) from 8f (1-[3-(Pyridin-2-ylmethoxymethyl)-phenyl]-1H-benzoimidazol-5-yl)-methanol (10a)

To a solution of compound 9a (250 mg, 0.65 mmol) in $CH_2Cl_2$ (10 mL) at −78° C. in a $N_2$ atmosphere was added a DIBAL solution in toluene (0.7 mL, 2.5 eqiv) and the reaction mixture was stirred for 2 hours. The reaction mixture was quenched with methanol (2 mL), and concentrated under reduced pressure. The residue was dissolved in $CH_2Cl_2$ (100 mL), washed with brine, dried over anhydrous $Na_2SO_4$ and concentrated under reduced pressure. The crude product was purified by column chromatography on silica gel using a 4:6 mixture of ethyl acetate and pet-ether as the eluent to afford compound 10a (150 mg, 67%) as a solid. Mp. 101-102.9° C.

In analogy herewith, the following compounds were prepared:

{1-[3-(1-Methyl-1H-imidazol-2-ylmethoxymethyl)-phenyl]-1H-benzoimidazol-5-yl}-methanol (10b) from 9b. LC-ESI-HRMS of [M+H]+ shows 349.1669 Da. Calc. 349.166425 Da, dev. 1.4 ppm {1-[3-(2-Methyl-2H-[1,2,4]triazol-3-ylmethoxymethyl)-phenyl]-1H-benzoimidazol-5-yl}-methanol (10c) from 9c. LC-ESI-HRMS of [M+H]+ shows 350.162 Da. Calc. 350.161625 Da, dev. 1.1 ppm {1-[3-(1,3-Thiazol-2-ylmethoxymethyl)-phenyl]-1H-benzoimidazol-5-yl}-methanol (10g) from 9g. LC-ESI-HRMS of [M+H]+ shows 352.112 Da. Calc. 352.111925 Da, dev. 0.2 ppm {1-[3-(2-Methyl-2H-pyrazol-3-ylmethoxymethyl)-phenyl]-1H-benzoimidazol-5-yl}-methanol (10e) from 9e. LC-ESI-HRMS of [M+H]+ shows 349.1662 Da. Calc. 349.166425 Da, dev. −0.6 ppm as are:

{1-[3-(Pyridin-3-ylmethoxymethyl)-phenyl]-1H-benzoimidazol-5-yl}-methanol (10d) from 9d.

{1-[3-(Pyrimidin-4-ylmethoxymethyl)-phenyl]-1H-benzoimidazol-5-yl}-methanol (10f) from 9f.

5-Methoxymethyl-1-[3-(pyridin-2-ylmethoxymethyl)-phenyl]-1H-benzoimidazole (11a)

To an ice-cold suspension of NaH (20 mg) in dry THF (10 mL) in a $N_2$ atmosphere was added a solution of compound 10a (100 mg, 0.3 mmol) in dry THF (2 mL). The reaction mixture was stirred at 0° C. for 30 min. Then methyl iodide (0.02 mL, 1 eqiv) was added and stirring was continued for 3 hours at RT. The reaction mixture was quenched with water, concentrated to remove THF and the residue was extracted with $CH_2Cl_2$ (3×30 mL) and dried over anhydrous $Na_2SO_4$. The solvent was removed under reduced pressure, and the crude product was purified by column chromatography on silica gel using a 3:7 mixture of ethyl acetate and pet-ether as the eluent to afford compound 11a (90 mg, 90%) as a liquid. LC-ESI-HRMS of [M+H]+ shows 360.1711 Da. Calc. 360.171125 Da, dev. −0.1 ppm In analogy herewith, the following compounds were prepared:

5-Methoxymethyl-1-[3-(1-methyl-1H-imidazol-2-ylmethoxymethyl)-phenyl]-1H-benzoimidazole (11b) from 10b. LC-ESI-HRMS of [M+H]+ shows 363.1812 Da. Calc. 363.182025 Da, dev. −2.3 ppm 5-Methoxymethyl-1-[3-(2-methyl-2H-[1,2,4]triazol-3-ylmethoxymethyl)-phenyl]-1H-benzoimidazole (11c) from 10c. LC-ESI-HRMS of [M+H]+ shows 364.1779 Da. Calc. 364.177325 Da, dev. 1.6 ppm 5-Methoxymethyl-1-[3-(2-methyl-2H-pyrazol-3-ylmethoxymethyl)-phenyl]-1H-benzoimidazole (11f) from 10f. LC-ESI-HRMS of [M+H]+ shows 363.1817 Da. Calc. 363.182025 Da, dev. −0.9 ppm 5-Methoxymethyl-1-[3-(1,3-thiazol-2-ylmethoxymethyl)-phenyl]-1H-benzoimidazole (11g) from 10g. LC-ESI-HRMS of [M+H]+ shows 366.1282 Da. Calc. 366.127625 Da, dev. 1.6 ppm as are:

5-Methoxymethyl-1-[3-(pyridin-3-ylmethoxymethyl)-phenyl]-1H-benzoimidazole (11d) from 10d 5-Methoxymethyl-1-[3-(pyrimidin-4-ylmethoxymethyl)-phenyl]-1H-benzoimidazole (11e) from 10e Example 4

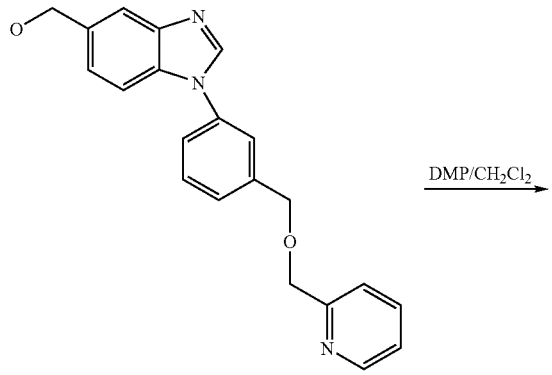

10a

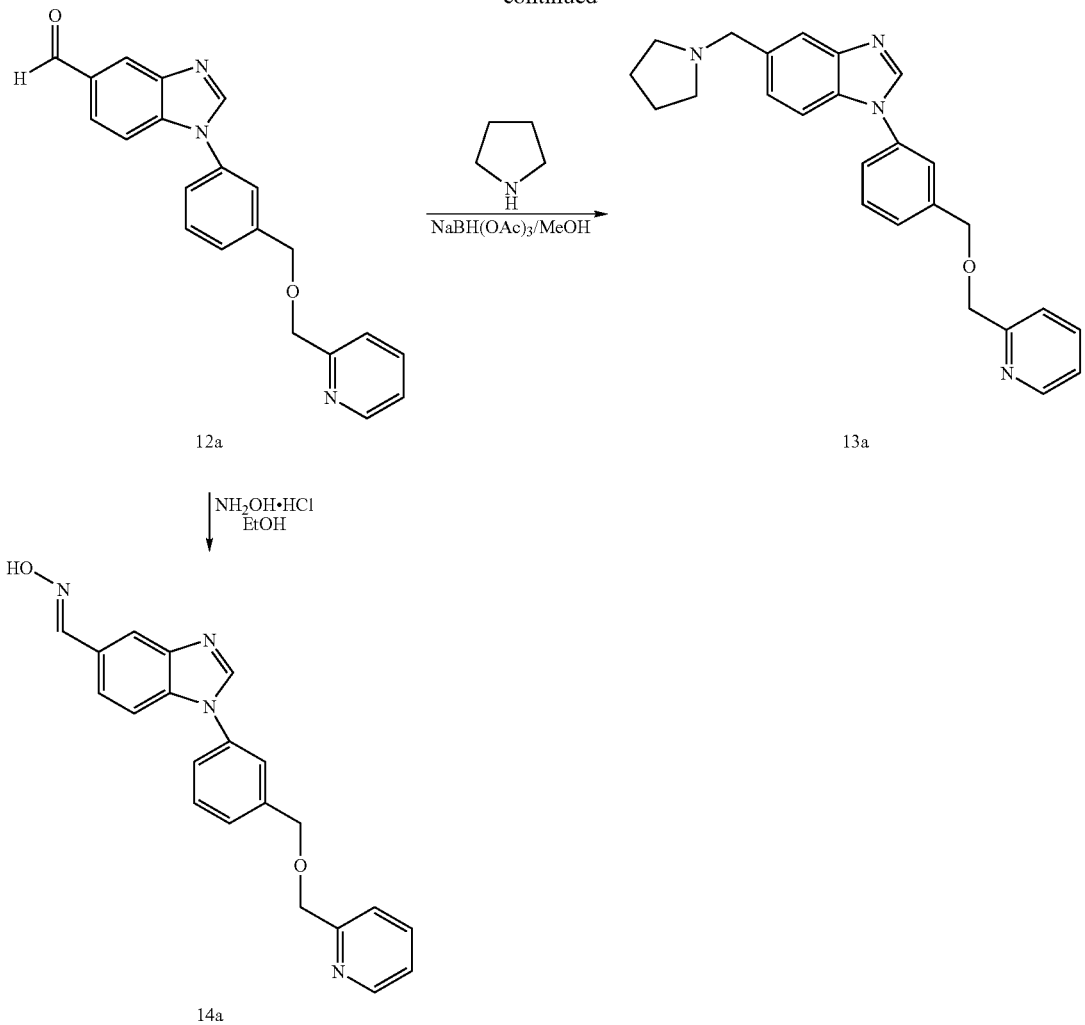

1-[3-(Pyridin-2-ylmethoxymethyl)-phenyl]-1H-benzoimidazole-5-carbaldehyde (12a)

To an ice-cold solution of compound 10a (320 mg, 0.92 mmol) in dry $CH_2Cl_2$ (10 mL) in a $N_2$ atmosphere was added Dess-Martin periodinane (DMP) (600 mg) portion wise and the reaction mixture was stirred for 3 hours at RT. The reaction mixture was quenched with solid $NaHCO_3$ at 0° C. The product was extracted with $CH_2Cl_2$ (3×30 mL) and the combined organic layers were dried over anhydrous $Na_2SO_4$ and evaporated under reduced pressure. The crude product was purified by column chromatography on silica gel using a 3:7 mixture of ethyl acetate and pet-ether as the eluent to afford compound 12a (220 mg) as a gum.

In analogy herewith, the following compounds were prepared:

1-[3-(1-Methyl-1H-imidazol-2-ylmethoxymethyl)-phenyl]-1H-benzoimidazole-5-carbaldehyde (12b)

1-[3-(2-Methyl-2H-[1,2,4]triazol-3-ylmethoxymethyl)-phenyl]-1H-benzoimidazole-5-carbaldehyde (12c)

1-[3-(2-Methyl-2H-pyrazol-3-ylmethoxymethyl)-phenyl]-1H-benzoimidazole-5-carbaldehyde (12e)

1-[3-(1,3-Thiazol-2-ylmethoxymethyl)-phenyl]-1H-benzoimidazole-5-carbaldehyde (12g)

as are:

1-[3-(Pyridin-3-ylmethoxymethyl)-phenyl]-1H-benzoimidazole-5-carbaldehyde (12d)

1-[3-(Pyrimidin-4-ylmethoxymethyl)-phenyl]-1H-benzoimidazole-5-carbaldehyde (12f)

1-[3-(Pyridin-2-ylmethoxymethyl)-phenyl]-5-pyrrolidin-1-ylmethyl-1H-benzoimidazole (13a)

A solution of compound 12a (80 mg, 0.15 mmol) and pyrrolidine (0.013 mL) in dichloromethane (10 mL) was stirred for 30 min at RT, then sodium triacetoxyboro-hydride (100 mg) was added to the reaction mixture at 0° C. The mixture was stirred for 12 hours at RT. The reaction mixture was quenched with water and the product was extracted with $CH_2Cl_2$ (3×40 mL). The combined organic layers were dried over anhydrous $Na_2SO_4$, the solvent was removed under reduced pressure and the crude product was purified by column chromatography on silica gel using a 3:7 mixture of ethyl acetate and pet-ether as the eluent to afford compound 13a (40 mg, 68%) as a solid. Mp 192-194° C.

In analogy herewith, the following compound was prepared:

1H-[3-(1-Methyl-1H-imidazol-2-ylmethoxymethyl)-phenyl]-5-pyrrolidin-1-ylmethyl-1H-benzoimidazole (13b) isolated as a yellowish gum. LC-ESI-HRMS of [M+H]+ shows 402.2312 Da. Calc. 402.229425 Da, dev. 4.4 ppm 1-[3-(Pyridin-2-ylmethoxymethyl)-phenyl]-1H-benzoimidazole-5-carbaldehyde oxime (14a)

To a solution of compound 12a (220 mg, 0.64 mmol) and pyridine (0.08 mL, 1.5 equiv) in ethanol (2 mL) was added hydroxylamine hydrochloride (500 mg) and the reaction mixture was stirred at RT for 3 hours. The reaction mixture was concentrated in vacuo and the residue was dissolved in ethyl acetate (100 mL), washed with brine, dried over anhydrous $Na_2SO_4$ and concentrated under reduced pressure. The crude product was purified by column chromatography on silica gel using a mixture of ethyl acetate and pet-ether as the eluent to afford compound 14a (180 mg, 78%) as a solid. Mp 154-154.8° C.

In analogy herewith, the following compounds were prepared:

1-[3-(1-Methyl-1H-imidazol-2-ylmethoxymethyl)-phenyl]-1H-benzoimidazole-5-carbaldehyde oxime (14b) from 12b. Mp 209.8-211.7° C.

and

1-[3-(2-Methyl-2H-[1,2,4]triazol-3-ylmethoxymethyl)-phenyl]-1H-benzoimidazole-5-carbaldehyde oxime (14c) from 12c. Mp 145.8-147.7° C.

O-Methyl 1-[3-(2-methyl-2H-[1,2,4]triazol-3-ylmethoxymethyl)-phenyl]-1H-benzoimidazole-5-carbaldehyde oxime (14h) from 12c and O-methyl hydroxylamine. LC-ESI-HRMS of [M+H]+ shows 377.1724 Da. Calc. 377.172525 Da, dev. −0.3 ppm 1-[3-(2-Methyl-2H-pyrazol-3-ylmethoxymethyl)-phenyl]-1H-benzoimidazole-5-carbaldehyde oxime (14e) from 12e. LC-ESI-HRMS of [M+H]+ shows 362.1603 Da. Calc. 362.161625 Da, dev. −3.7 ppm O-Methyl 1-[3-(2-methyl-2H-pyrazol-3-ylmethoxymethyl)-phenyl]-1H-benzoimidazole-5-carbaldehyde oxime (14i) from 12e and O-methyl hydroxyl amine. LC-ESI-HRMS of [M+H]+ shows 376.1755 Da. Calc. 376.177325 Da, dev. −4:9 ppm 1-[3-(1,3-Thiazol-2-ylmethoxymethyl)-phenyl]-1H-benzoimidazole-5-carbaldehyde oxime (14j) from 12g. LC-ESI-HRMS of [M+H]+ shows 365.1074 Da. Calc. 365.107225 Da, dev. 0.5 ppm O-Methyl 1-[3-(1,3-thiazol-2-ylmethoxymethyl)-phenyl]-1H-benzoimidazole-5-carbaldehyde oxime (14g) from 12g and O-methyl hydroxylamine. LC-ESI-HRMS of [M+H]+ shows 379.1238 Da. Calc. 379.122825 Da, dev. 2.6 ppm and 1-[3-(Pyridin-3-ylmethoxymethyl)-phenyl]-1H-benzoimidazole-5-carbaldehyde oxime (14d)

1-[3-(Pyrimidin-4-ylmethoxymethyl)-phenyl]-1H-benzoimidazole-5-carbaldehyde oxime (14f)

are prepared likewise.

Example 5

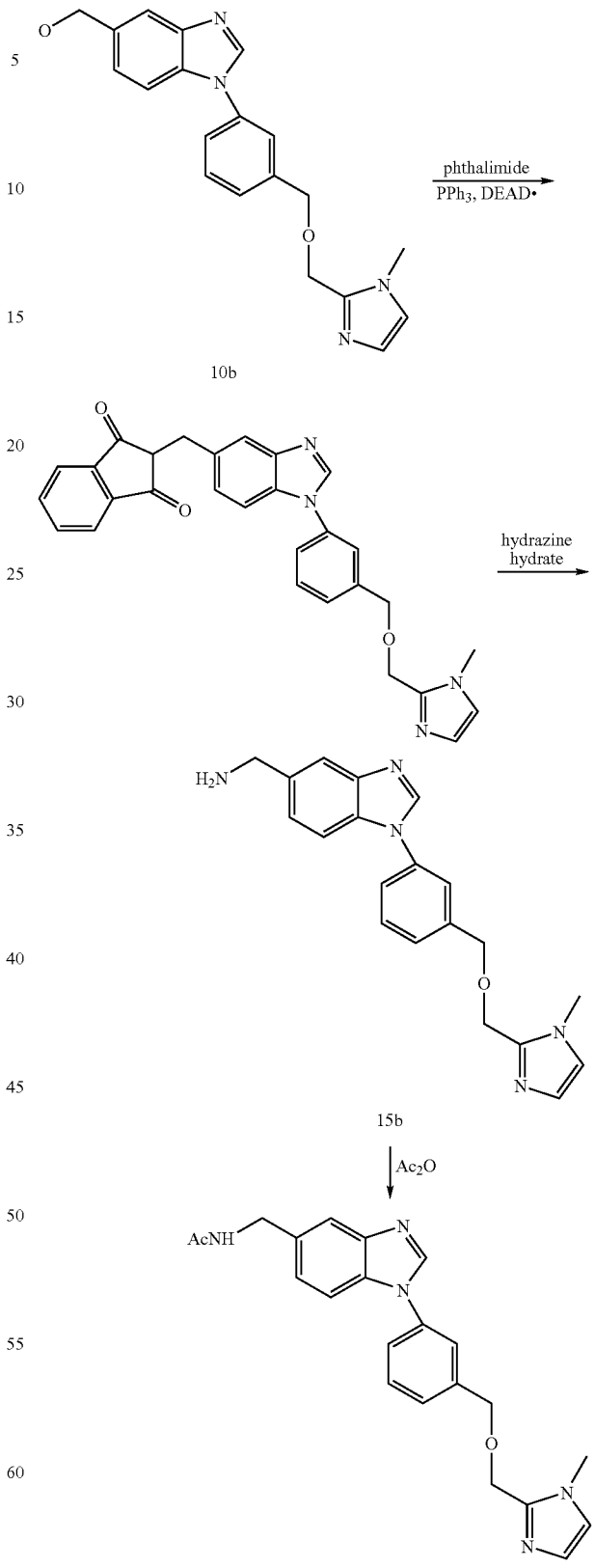

C-{1-[3-(1-Methyl-1H-imidazol-2-ylmethoxymethyl)-phenyl]-1H-benzoimidazol-5-yl}-methylamine (15b)

Compound 10b was reacted with phthalimide in the presence of triphenylphosphine and diethyl azodicarboxylate (DEAD) under standard Mitsunobu conditions to afford the alkylated phthalimide, which in turn was cleaved with hydrazine hydrate in ethanol to afford 15b. LC-ESI-HRMS of [M+H]+ shows 348.1832 Da. Calc. 348.182425 Da, dev. 2.2 ppm In analogy herewith, C-{1-[3-(Pyridin-2-ylmethoxymethyl)-phenyl]-1H-benzoimidazol-5-yl}-methylamine (15a) was prepared from 10a. LC-ESI-HRMS of [M+H]+ shows 345.1733 Da. Calc. 345.171525 Da, dev. 5.1 ppm

N-{1-[3-(1-Methyl-1H-imidazol-2-ylmethoxymethyl)-phenyl]-1H-benzoimidazol-5-ylmethyl}-acetamide (16b)

Compound 15b was acetylated with acetic anhydride under standard conditions to afford compound 16b. LC-ESI-HRMS of [M+H]+ shows 390.1926 Da. Calc. 390.192925 Da, dev. −0.8 ppm In analogy herewith, the following compounds were prepared:

N-{1-[3-(Pyridin-2-ylmethoxymethyl)-phenyl]-1H-benzoimidazol-5-ylmethyl}-acetamide (16a) from 15a. LC-ESI-HRMS of [M+H]+ shows 387.1809 Da. Calc. 387.182025 Da, dev. −2.9 ppm N-{1-[3-(2-methyl-2H-[1,2,4]triazol-3-ylmethoxymethyl)-phenyl]-1H-benzoimidazol-5-ylmethyl}-acetamide (16c) from 15c. LC-ESI-HRMS of [M+H]+ shows 391.1876 Da. Calc. 391.188249 Da, dev. −1.7 ppm N-{1-[3-(2-Methyl-2H-pyrazol-3-ylmethoxymethyl)-phenyl]-1H-benzoimidazole-5-ylmethyl}-acetamide (16e) from 15e. LC-ESI-HRMS of [M+H]+ shows 390.1928 Da. Calc. 390.192925 Da, dev. −0.3 ppm N-{1-[3-(1,3-Thiazol-2-ylmethoxymethyl)-phenyl]-1H-benzoimidazole-5-ylmethyl}-acetamide (16g) from 15g. LC-ESI-HRMS of [M+H]+ shows 393.1382 Da. Calc. 393.138522 Da, dev. −0.8 ppm

Example 6

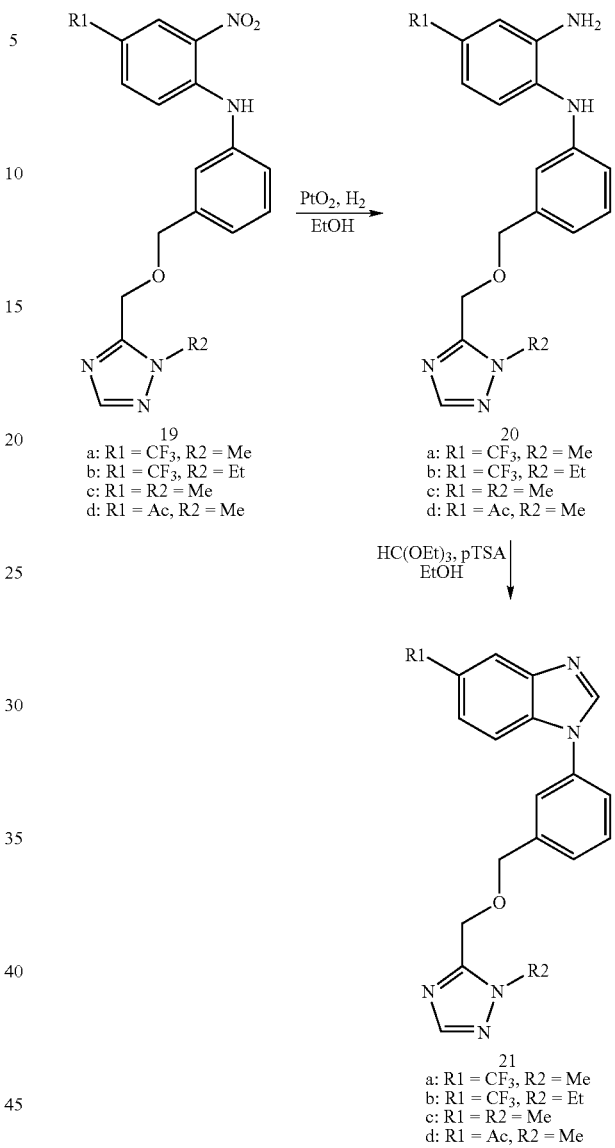

3-(1-Ethyl-1H-imidazol-2-ylmethoxymethyl)-phenylamine (18b)

To a stirred solution of (1-ethyl-1H-imidazol-2-yl)-methanol (1.3 g, 10.2 mmol) in DMF (10 ml) was added sodium hydride (0.49 g 60% dispersion in mineral oil). When the evolution of hydrogen had ceased, 3-nitrobenzylbromide (2.21 g, 10.2 mmol) was added and stirring was continued at ambient temperature for 1 hour. Ice was added and the resultant mixture was extracted with ethyl acetate. The organic extract was dried over magnesium sulphate and concentrated in vacuo. This concentrate was dissolved in ethanol (20 ml). Platinum oxide (0.2 g) was added and the mixture was hydrogenated until the hydrogen uptake had ceased. Filtration through celite and evaporation of the filtrate left 18b (1.7 g, 72%) as a yellowish oil.

3-(1-Methyl-1H-imidazol-2-ylmethoxymethyl)-phenylamine (18a) was prepared analogously from (1-methyl-1H-imidazol-2-yl)-methanol.

[3-(2-Methyl-2H-[1,2,4]triazol-3-ylmethoxymethyl)-phenyl]-(2-nitro-4-trifluoromethyl-phenyl)-amine (19a)

To a solution of compound 18a (1.0 g, 4.9 mmol) in anhydrous NMP (10 ml) was added triethylamine (0.68 ml, 4.9 mmol) and compound 17a (0.68 ml, 4.91 mmol) and the resultant mixture was stirred at 100° C. over night. The cooled reaction mixture was poured into ice-water and the precipitate was filtered off, re-dissolved in dichloromethane, dried over magnesium sulphate and concentrated in vacuo. This concentrate was triturated in a mixture of diethyl ether and petroleum ether to afford 19a as a brownish solid (1.2 g, 62%).

The following compounds were prepared in analogy herewith:

[3-(2-Ethyl-2H-[1,2,4]triazol-3-ylmethoxymethyl)-phenyl]-(2-nitro-4-trifluoromethylphenyl)-amine (19b) from 17a and 18b. Yield: 78%

(4-Methyl-2-nitro-phenyl)-[3-(2-methyl-2H-[1,2,4]triazol-3-ylmethoxymethyl)-phenyl]-amine (19c) from 17b and 18a. Yield: 20%

1-{4-[3-(2-Methyl-2H-[1,2,4]triazol-3-ylmethoxymethyl)-phenylamino]-3-nitro-phenyl}-ethanone (19d) from 17c and 18a. Yield: 74%

$N^1$-[3-(2-Methyl-2H-[1,2,4]triazol-3-ylmethoxymethyl)-phenyl]-4-trifluoromethyl-benzene-1,2-diamine (20a)

To a solution of 19a (0.6 g, 1.5 mmol) in ethanol (20 ml) was added platinum oxide (0.15 g) and the resultant mixture was hydrogenated at ambient pressure until the hydrogen uptake had ceased. Filtration through celite and concentration of the filtrate in vacuo left 20a, which was taken directly into the next step.

The following compounds were prepared in analogy herewith:

$N^1$-[3-(2-Ethyl-2H-[1,2,4]triazol-3-ylmethoxymethyl)-phenyl]-4-trifluoromethyl-benzene-1,2-diamine (20b) from 19b 4-Methyl-$N^1$-[3-(2-methyl-2H-[1,2,4]triazol-3-ylmethoxymethyl)-phenyl]-benzene-1,2-diamine (20c) from 19c 1-{3-Amino-4-[3-(2-methyl-2H-[1,2,4]triazol-3-ylmethoxymethyl)-phenylamino]-phenyl}-ethanone (20d) from 19d 1-[3-(2-Methyl-2H-[1,2,4]triazol-3-ylmethoxymethyl)-phenyl]-5-trifluoromethyl-1H-benzoimidazole (21a)

To a solution of compound 20a in anhydrous THF (15 ml) was added triethyl orthoformate (0.75 ml, 4.4 mmol) and a catalytic amount of p-toluenesulphonic acid. The resultant mixture was stirred at reflux for 1 hour. The solvent was removed in vacuo and the residue was purified by column chromatography on silica gel, eluting with a mixture of ethyl acetate and methanol (9:1 v/v). Compound 21a (0.87 g) was precipitated as the hydro chloride by addition of etheral hydrogen chloride to the pure fractions. LC-ESI-HRMS of [M+H]+ shows 388.14 Da. Calc. 388.138519 Da, dev. 3.8 ppm The following compounds were prepared in analogy herewith:

1-[3-(2-Ethyl-2H-[1,2,4]triazol-3-ylmethoxymethyl)-phenyl]-5-trifluoromethyl-1H-benzoimidazole (21b) from compound 20b. Yield: 67%. LC-ESI-HRMS of [M+H]+ shows 402.1548 Da. Calc. 402.154169 Da, dev. 1.6 ppm 5-Methyl-1-[3-(2-methyl-2H-[1,2,4]triazol-3-ylmethoxymethyl)-phenyl]-1H-benzoimidazole (21c) from compound 20c. Yield: 7% (3 steps). LC-ESI-HRMS of [M+H]+ shows 334.1679 Da. Calc. 334.166785 Da, dev. 3.3 ppm 1-{1-[3-(2-Methyl-2H-[1,2,4]triazol-3-ylmethoxymethyl)-phenyl]-1H-benzoimidazol-5-yl}-ethanone (21d) from compound 20d. Yield: 53% isolated as the free base. Mp 121.4-123.6° C.

Example 7

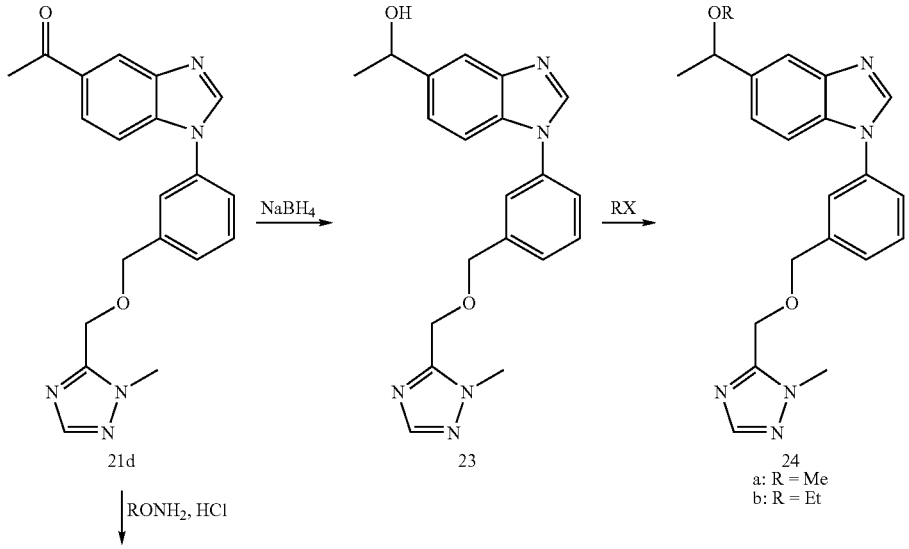

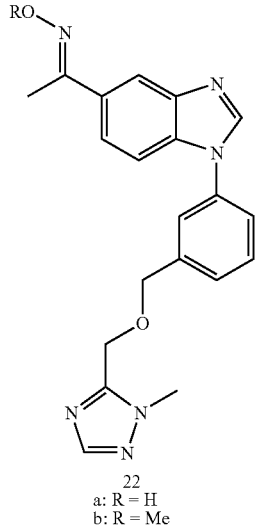

22
a: R = H
b: R = Me

1-{1-[3-(2-Methyl-2H-[1,2,4]triazol-3-ylmethoxymethyl)-phenyl]-1H-benzoimidazol-5-yl}-ethanone oxime (22a)

A suspension of 21d (2.34 g, 6.47 mmol) in ethanol (50 ml) was stirred at reflux. Hydroxylamine, hydrochloride (0.68 g, 9.71 mmol) was added and stirring was continued for 45 min, whereafter the solvent was removed in vacuo. The residue was triturated in water to afford compound 22a as the hydro chloride. Yield: 54%. Mp 178.8-180.4° C.

1-(1-[3-(2-Methyl-2H-[1,2,4]triazol-3-ylmethoxymethyl)-phenyl]-1H-benzoimidazol-5-yl)-ethanone O-ethyl-oxime (22b)

This was prepared analogously from compound 21d and O-ethyl hydroxylamine. Yield: 56%. Mp 130.2-134.3° C.

1-{1-[3-(2-Methyl-2H-[1,2,4]triazol-3-ylmethoxymethyl)-phenyl]-1H-benzoimidazol-5-yl}-ethanone O-methyl-oxime (22c)

This was prepared analogously from compound 21d and O-methyl hydroxylamine. Yield: 58.3%. LC-ESI-HRMS of [M+H]+ shows 391.1874 Da. Calc. 391.188225 Da, dev. −2.1 ppm

1{-1-[3-(2-Methyl-2H-[1,2,4]triazol-3-ylmethoxymethyl)-phenyl]-1H-benzoimidazol-5-yl}-ethanol (23)

To a solution of compound 21d (4.9 g, 13.9 mmol) in a mixture of DMF (90 ml) and methanol (10 ml) was added sodium boronhydride (0.53 g, 13.9 mmol). The resultant mixture was stirred at 60° C. for 1 hour. The cooled mixture was partitioned between water and ethyl acetate. The organic layer was washed with brine, dried over magnesium sulphate and eluted through silica gel with a mixture of ethyl acetate and methanol (9:1 v/v). The pure fractions were concentrated and compound 23 was precipitated as the hydro chloride upon addition of etheral hydrogen chloride to the concentrate. Yield: 46%. LC-ESI-HRMS of [M+H]+ shows 364.1764 Da. Calc. 364.177325 Da, dev. −2.5 ppm

5-(1-Methoxy-ethyl)-1-[3-(2-methyl-2H-[1,2,4]triazol-3-ylmethoxymethyl)-phenyl]-1H-benzoimidazole (24a)

To a solution of compound 23, free base (0.54 g, 1.49 mmol) in anhydrous DMF (10 ml) was added sodium hydride (1.78 mmol, 70 mg 60% dispersion in mineral oil) and the resultant mixture was stirred at ambient temperature, until the evolution of hydrogen had ceased. Iodomethane (0.2 ml, 2.98 mmol) was added and stirring was continued for 3 hours. The solvent was evaporated in vacuo and the residue was purified by column chromatography on silica gel, eluting with a mixture of ethyl acetate and methanol (4:1 v/v). Compound 24a was isolated as the hydrochloride by addition of etheral hydrogen chloride to a concentrate of the pure fractions. Yield: 20%. LC-ESI-HRMS of [M+H]+ shows 378.1909 Da. Calc. 378.192925 Da, dev. −5.4 ppm

5-(1-Ethoxy-ethyl)-1-[3-(2-methyl-2H-[1,2,4]triazol-3-ylmethoxymethyl)-phenyl]-1H-benzoimidazole (24b)

This was prepared analogously from compound 23 and iodoethane. Yield: 54%. LC-ESI-HRMS of [M+H]+ shows 392.2102 Da. Calc. 392.208625 Da, dev. 4 ppm

Example 8

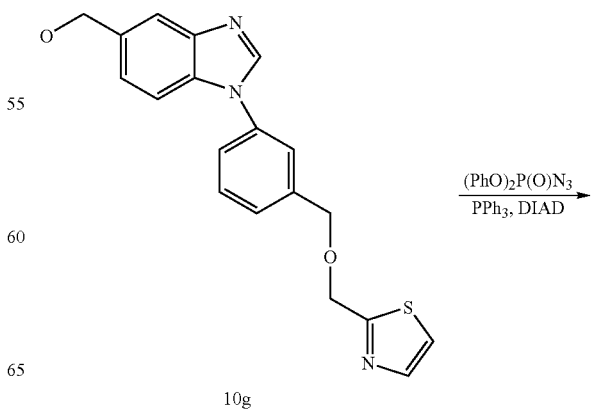

10g

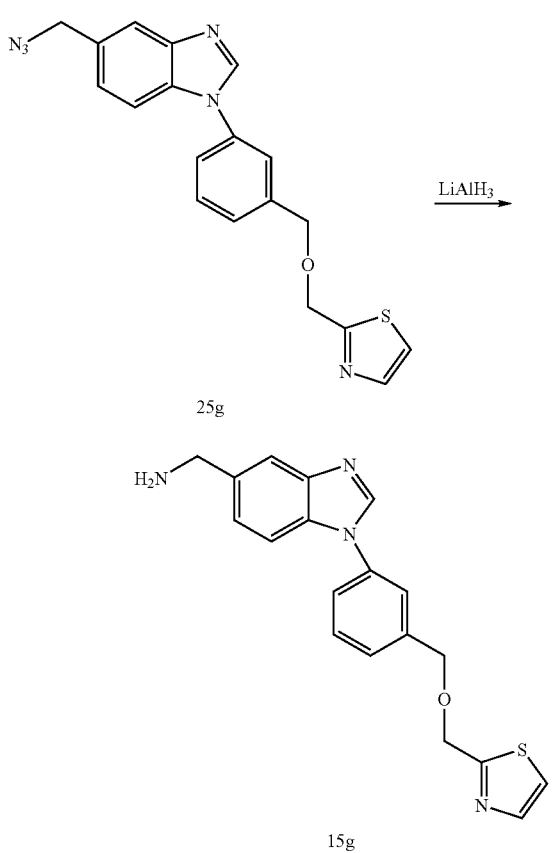

5-Azidomethyl-1-[3-(thiazol-2-ylmethoxymethyl)-phenyl]-1H-benzoimidazole (25g)

To a mixture of 10g (0.1 g; 0.28 mmol) and PPh₃ (0.11 g; 0.43 mmol) in THF (3 ml) was added DIAD (0.09 g; 0.43 mmol) at 0° C. After 5 min. diphenylphosphorylazide (0.12 g; 0.43 mmol) was added and the mixture was allowed to reach room temperature. Stirring was continued for 2 hours. The solvent was removed by evaporation and the residue was eluted through silica gel with a mixture of dichloromethane and methanol (50:1 v/v) to afford 25g. LC-ESI-HRMS of [M+H]+ shows 377.1188 Da. Calc. 377.118455 Da, dev. 0.9 ppm In analogy herewith the following compounds were prepared 5-Azidomethyl-1-[3-(2-methyl-2H-[1,2,4]triazol-3-yl-methoxymethyl)-phenyl]-1H-benzoimidazole (25c) from 10c. LC-ESI-HRMS of [M+H]+ shows 375.1671 Da. Calc. 375.168182 Da, dev. −2.9 ppm 5-Azidomethyl-1-[3-(2-methyl-2H-pyrazol-3-ylmethoxymethyl)-phenyl]-1H-benzoimidazole (25e) from 10e. LC-ESI-HRMS of [M+H]+ shows 374.1732 Da. Calc. 374.172925 Da, dev. 0.7 ppm C-{1-[3-(1,3-Thiazol-2-ylmethoxymethyl)-phenyl]-1H-benzoimidazole-5-yl}-methylamine (15g)

To a stirred solution of LiAlH₄ (40 mg) in anhydrous THF (4 ml) was added a solution of 25 g (200 mg) in anhydrous THF (4 ml) at 0° C. The resultant mixture was stirred at ambient temperature for 12 hours and then quenched with 3M NaOH and water, successively. Work-up of the organic layer afforded 15g (70 mg). LC-ESI-HRMS of [M+H]+ shows 351.1291 Da. Calc. 351.127925 Da, dev. 3.3 ppm In analogy herewith the following compounds were prepared C-{1-[3-(2-Methyl-2H-[1,2,4]triazol-3-ylmethoxymethyl)-phenyl]-1H-benzoimidazol-5-yl}-methylamine (15c) from 25c. LC-ESI-HRMS of [M+H]+ shows 349.1793 Da. Calc. 349.177684 Da, dev. 4.6 ppm C-{1-[3-(2-Methyl-2H-pyrazol-3-ylmethoxymethyl)-phenyl]-1H-benzoimidazole-5-yl}-methylamine (15e) from 25e. LC-ESI-HRMS of [M+H]+ shows 348.1828 Da. Calc. 348.182435 Da, dev. 1 ppm Example 9

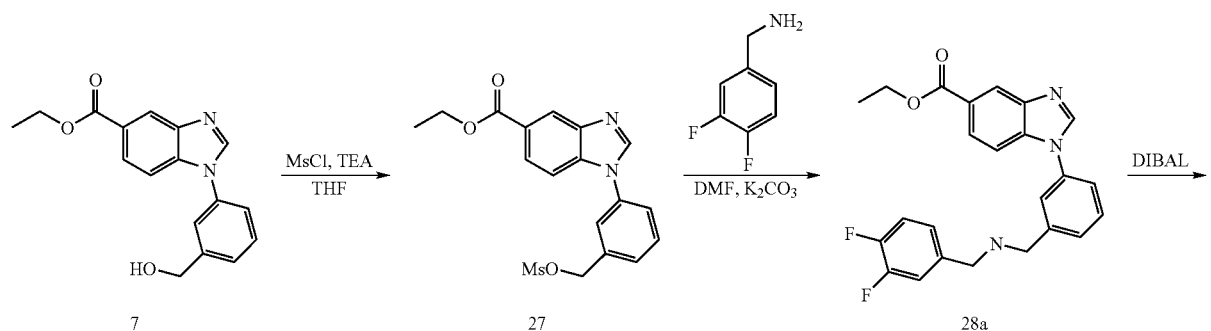

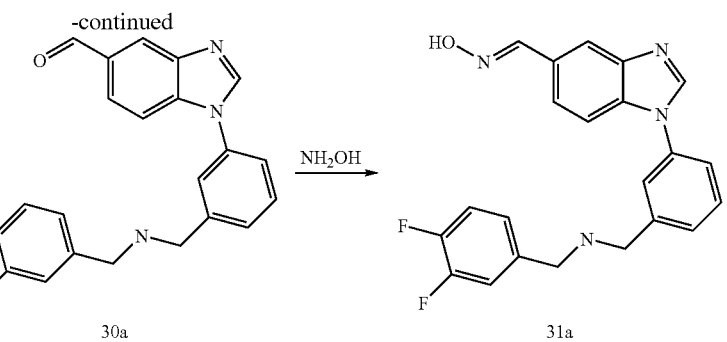
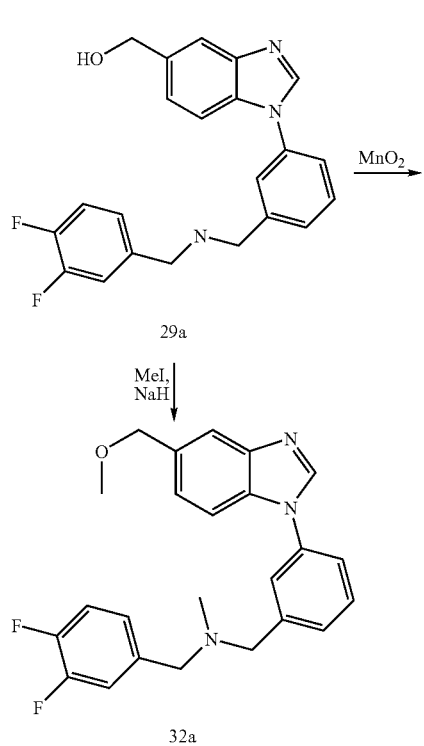

1-{3-[(3,4-Difluoro-benzylamino)-methyl]-phenyl}-1H-benzoimidazole-5-carboxylic acid ethyl ester (28a)

Compound 27 was prepared from compound 7 by the method described in Example 2. To a solution of compound 27 (3 g, 1.01 mmol) in DMF (30 ml) was added potassium carbonate (2 g; 1.45 mmol) and 3,4-difluorobenzylamine (1.43 ml; 1.2 mmol) and the resultant mixture was stirred at ambient conditions over night. Aqueous work-up followed by column chromatography afforded compound 28a (0.9 g). LC-ESI-HRMS of [M+H]+ shows 422.1697 Da. Calc. 422.167925 Da, dev. 4.2 ppm In analogy herewith, the following compounds were prepared:

1-(3-{[(Pyridin-2-ylmethyl)-amino]-methyl}-phenyl)-1H-benzoimidazole-5-carboxylic acid ethyl ester (28b). LC-ESI-HRMS of [M+H]+ shows 387.1815 Da. Calc. 387.182025 Da, dev. −1.4 ppm 1-(3-{[(Pyridin-4-ylmethyl)-amino]-methyl}-phenyl)-1H-benzoimidazole-5-carboxylic acid ethyl ester (28c). LC-ESI-HRMS of [M+H]+ shows 387.182 Da. Calc. 387.182025 Da, dev. −0.1 ppm 1-(3-{[(Pyridin-3-ylmethyl)-amino]-methyl}-phenyl)-1H-benzoimidazole-5-carboxylic acid ethyl ester (28d). LC-ESI-HRMS of [M+H]+ shows 387.1814 Da. Calc. 387.182025 Da, dev. −1.6 ppm and 1-{3-[(3,4-Dichloro-benzylamino)-methyl]-phenyl}-1H-benzoimidazole-5-carboxylic acid ethyl ester (28e). LC-ESI-HRMS of [M+H]+ shows 454.1073 Da. Calc. 454.108825 Da, dev. −3.4 ppm (1-{3-[(3,4-Difluoro-benzylamino)-methyl]-phenyl}-1H-benzoimidazol-5-yl)-methanol (29a). Compound 28a was treated with DIBAL as described in Example 3 to afford compound 29a. LC-ESI-HRMS of [M+H]+ shows 380.1573 Da. Calc. 380.157443 Da, dev. −0.4 ppm (3,4-Difluoro-benzyl)-[3-(5-methoxymethyl-benzoimidazol-1-yl)-benzyl]-methylamine (32a). Compound 29a was treated with sodium hydride and iodomethane under standard conditions to afford the dimethylated product 32a. LC-ESI-HRMS of [M+H]+ shows 408.1896 Da. Calc. 408.188743 Da, dev. 2.1 ppm 1-{3-[(3,4-Difluoro-benzylamino)-methyl]-phenyl}-1H-benzoimidazole-5-carbaldehyde (30a). To a solution of compound 29a (0.2 g; 0.53 mmol) in dichloromethane (20 ml) was added manganese dioxide (0.69 g) in portions at 0° C. The resultant mixture was stirred at ambient temperature for 3 hours prior to filtration through celite. The filtrate was concentrated under reduced pressure and the residue was eluted through silica gel with a mixture of dichloromethane and methanol (9:1, v/v) to afford 30a. (170 mg).

1-{3-[(3,4-Difluoro-benzylamino)-methyl]-phenyl}-1H-benzoimidazole-5-carbaldehyde oxime (31a). To an ice-cooled solution of compound 30a (170 mg, 0.45 mmol) in ethanol (15 ml) was added pyridine (0.05 ml) and hydroxylamine, hydrochloride (31 mg) and the resultant mixture was stirred at ambient conditions over night. The reaction mixture was concentrated under reduced pressure and the residue was partitioned between dichloromethane and water. The organic layer was washed with brine, dried over sodium sulphate and evaporated to dryness. The residue was triturated in diethyl ether to afford compound 31a (70 mg). Mp 165-167° C.

Test Methods

In vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$$IC_{50} = \text{(applied test substance concentration, µM)} \times \frac{1}{\left(\frac{C_o}{C_x} - 1\right)}$$

where
$C_o$ is specific binding in control assays, and
$C_x$ is the specific binding in the test assay.
(The calculations assume normal mass-action kinetics).

Test results from these experiments with a number of compounds of the invention are shown in Table 1 below.

TABLE 1

| Test compound | In vitro binding $IC_{50}$ (µM) |
| --- | --- |
| Compound 22a | 0.0021 |
| Compound 23 | 0.022 |
| Compound 24b | 0.0092 |

The invention claimed is:

1. A compound of the general formula (I):

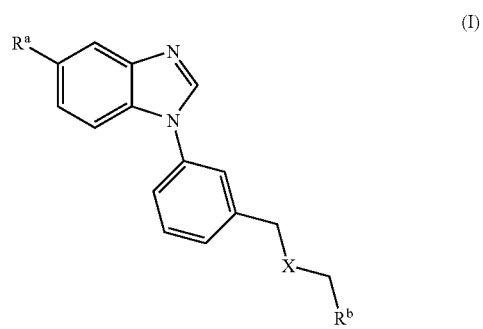

or an N-oxide thereof, any of its stereoisomers or any mixture of its stereoisomers,
or a pharmaceutically acceptable salt thereof,
wherein
$R^a$ represents halo, trifluoromethyl, trifluoromethoxy, cyano, nitro, $R^c$, $R^cO—$, $R^cO$-alkyl-, $R^c—O—N=(CR^d)—$, $R^c—(C=O)—$, $R^c—(C=O)$-alkyl-, $R^c—(C=O)—(NR^d)—$, $R^c—(C=O)—(NR^d)$-alkyl-, or $R^c—O—(C=O)—$;
  wherein $R^c$ is hydrogen, alkyl, cycloalkyl, cycloalkylakyl, alkenyl, or alkynyl; which alkyl, cycloalkyl, cycloalkylakyl, alkenyl, and alkynyl is optionally substituted with one or more azido or R'R"N—;
  wherein R' and R" independent of each other are hydrogen or alkyl or R' and R" together with the together with the nitrogen to which they are attached form a pyrrolidine or piperidine ring;
  $R^d$ is hydrogen or alkyl;
$R^b$ represents an aryl or a heteroaryl group;
  which aryl or heteroaryl group is optionally substituted with one or more substituents independently selected from the group consisting of:
    halo, hydroxy, R'''R''''N—, R'''R''''N-alkyl, cyano, nitro, trifluoromethyl, trifluoromethoxy, alkoxy, cycloalkoxy, alkyl, cycloalkyl, cycloalkylalkyl, alkenyl, and alkynyl;
    wherein R''' and R'''' independent of each other are hydrogen or alkyl; and
X represents —O—, $NR^e$;
  wherein $R^e$ represents hydrogen or alkyl.

2. The compound of claim 1, or an N-oxide thereof, any of its stereoisomers or any mixture of its stereoisomers, or a pharmaceutically acceptable salt thereof, wherein $R^a$ represents trifluoromethyl.

3. The compound of claim 1, or an N-oxide thereof, any of its stereoisomers or any mixture of its stereoisomers, or a pharmaceutically acceptable salt thereof, wherein $R^a$ represents $R^c$ or $R^cO$-alkyl-, wherein $R^c$ represents hydrogen or alkyl.

4. The compound of claim 1, or an N-oxide thereof, any of its stereoisomers or any mixture of its stereoisomers, or a pharmaceutically acceptable salt thereof, wherein $R^a$ represents alkyl substituted with azido or R'R"N-alkyl-.

5. The compound of claim 1, or an N-oxide thereof, any of its stereoisomers or any mixture of its stereoisomers, or a pharmaceutically acceptable salt thereof, wherein $R^a$ represents $R^c—O—N=(CR^d)—$, wherein $R^c$ represents hydrogen or alkyl and $R^d$ represents hydrogen or alkyl.

6. The compound of claim 1, or an N-oxide thereof, any of its stereoisomers or any mixture of its stereoisomers, or a pharmaceutically acceptable salt thereof, wherein $R^a$ represents $R^c$—(C=O)— or $R^c$—O—(C=O)—, wherein $R^c$ represents hydrogen or alkyl.

7. The compound of claim 1, or an N-oxide thereof, any of its stereoisomers or any mixture of its stereoisomers, or a pharmaceutically acceptable salt thereof, wherein $R^a$ represents $R^c$—(C=O)—(NR$^d$)— or $R^c$—(C=O)—(NR$^d$)-alkyl-, wherein $R^c$ represents hydrogen or alkyl and $R^d$ represents hydrogen.

8. The compound of claim 1, or an N-oxide thereof, any of its stereoisomers or any mixture of its stereoisomers, or a pharmaceutically acceptable salt thereof, wherein X represents —O—.

9. The compound of claim 1, or an N-oxide thereof, any of its stereoisomers or any mixture of its stereoisomers, or a pharmaceutically acceptable salt thereof, wherein X represents NR$^e$; wherein $R^e$ represents hydrogen or alkyl.

10. The compound of claim 1, or an N-oxide thereof, any of its stereoisomers or any mixture of its stereoisomers, or a pharmaceutically acceptable salt thereof, wherein $R^b$ represents an optionally substituted phenyl.

11. The compound of claim 1, or an N-oxide thereof, any of its stereoisomers or any mixture of its stereoisomers, or a pharmaceutically acceptable salt thereof, wherein $R^b$ represents a heteroaryl group selected from the group of triazolyl, pyridyl, imidazolyl, pyrazolyl, pyrimidyl and thiazolyl; and which heteroaryl group is optionally substituted with one or more substituents.

12. The compound of claim 1, which is
1-[3-(Pyridin-2-ylmethoxymethyl)-phenyl]-1H-benzoimidazole-5-carboxylic acid ethyl ester;
1-[3-(1-Methyl-1H-imidazol-2-ylmethoxymethyl)-phenyl]-1H-benzoimidazole-5-carboxylic acid ethyl ester;
1-[3-(2-Methyl-2H-pyrazol-3-ylmethoxymethyl)-phenyl]-1H-benzoimidazole-5-carboxylic acid ethyl ester;
1-[3-(2-Methyl-2H-[1,2,4]triazol-3-ylmethoxymethyl)-phenyl]-1H-benzoimidazole-5-carboxylic acid ethyl ester;
1-[3-(1,3-Thiazol-2-ylmethoxymethyl)phenyl]-1H-benzoimidazole-5-carboxylic acid ethyl ester;
1-[3-(Pyridin-3-ylmethoxymethyl)-phenyl]-1H-benzoimidazole-5-carboxylic acid ethyl ester;
1-[3-(Pyrimidin-4-ylmethoxymethyl)-phenyl]-1H-benzoimidazole-5-carboxylic acid ethyl ester;
{1-[3-(Pyridin-2-ylmethoxymethyl)-phenyl]-1H-benzoimidazol-5-yl}-methanol;
{1-[3-(1-Methyl-1H-imidazol-2-ylmethoxymethyl)-phenyl]-1H-benzoimidazol-5-yl}-methanol;
{1-[3-(2-Methyl-2H-[1,2,4]triazol-3-ylmethoxymethyl)-phenyl]-1H-benzoimidazol-5-yl}-methanol;
{1-[3-(1,3-Thiazol-2-ylmethoxymethyl)-phenyl]-1H-benzoimidazol-5-yl}-methanol;
{1-[3-(2-Methyl-2H-pyrazol-3-ylmethoxymethyl)-phenyl]-1H-benzoimidazol-5-yl}-methanol;
{1-[3-(Pyridin-3-ylmethoxymethyl)-phenyl]-1H-benzoimidazol-5-yl}-methanol;
{1-[3-(2-Methyl-2H-pyrazol-3-ylmethoxymethyl)-phenyl]-1H-benzoimidazol-5-yl}-methanol;
{1-[3-(Pyrimidin-4-ylmethoxymethyl)-phenyl]-1H-benzoimidazol-5}-methanol;
5-Methoxymethyl-1-[3-(pyridin-2-ylmethoxymethyl)-phenyl]-1H-benzoimidazole;
5-Methoxymethyl-1-[3-(1-methyl-1H-imidazol-2-ylmethoxymethyl)-phenyl]-1H-benzoimidazole;
5-Methoxymethyl-1-[3-(2-methyl-2H-[1,2,4]-triazol-3-ylmethoxymethyl)-phenyl]-1H-benzoimidazole;
5-Methoxymethyl-1-[3-(2-methyl-2H-pyrazol-3-ylmethoxymethyl)-phenyl]-1H-benzoimidazole;
5-Methoxymethyl-1-[3-(1,3-thiazol-2-ylmethoxymethyl)-phenyl]-1H-benzoimidazole;
5-Methoxymethyl-1-[3-(pyridin-3-ylmethoxymethyl)-phenyl]-1H-benzoimidazole;
5-Methoxymethyl-1-[3-(pyrimidin-4-ylmethoxymethyl)-phenyl]-1H-benzoimidazole;
1-[3-(Pyridin-2-ylmethoxymethyl)-phenyl]-5-pyrrolidin-1-ylmethyl-1H-benzoimidazole;
1-[3-(1-Methyl-1H-imidazol-2-ylmethoxymethyl)-phenyl]-5-pyrrolidin-1-ylmethyl-1H-benzoimidazole;
1-[3-(Pyridin-2-ylmethoxymethyl)-phenyl]-1H-benzoimidazole-5-carbaldehyde oxime;
1-[3-(1-Methyl-1H-imidazol-2-ylmethoxymethyl)-phenyl]-1H-benzoimidazole-5-carbaldehyde oxime;
1-[3-(2-Methyl-2H-[1,2,4]triazol-3-ylmethoxymethyl)-phenyl]-1H-benzoimidazole-5-carbaldehyde oxime;
O-Methyl 1-[3-(2-methyl-2H-[1,2,4]-triazol-3-ylmethoxymethyl)-phenyl]-1H-benzoimidazole-5-carbaldehyde oxime;
1-[3-(2-Methyl-2H-pyrazol-3-ylmethoxymethyl)-phenyl]-1H-benzoimidazole-5-carbaldehyde oxime;
O-Methyl 1-[3-(2-methyl-2H-pyrazol-3-ylmethoxymethyl)-phenyl]-1H-benzoimidazole-5-carbaldehyde oxime;
1-[3-(1,3-Thiazol-2-ylmethoxymethyl)-phenyl]-1H-benzoimidazole-5-carbaldehyde oxime;
O-Methyl 1-[3-(1,3-thiazol-2-ylmethoxymethyl)-phenyl]-1H-benzoimidazole-5-carbaldehyde oxime;
1-[3-(Pyridin-3-ylmethoxymethyl)-phenyl]-1H-benzoimidazole-5-carbaldehyde oxime;
1-[3-(Pyrimidin-4-ylmethoxymethyl)-phenyl]-1H-benzoimidazole-5-carbaldehyde oxime;
C-{1-[3-(1-Methyl-1H-imidazol-2-ylmethoxymethyl)-phenyl]-1H-benzoimidazol-5-yl}-methylamine;
C-{1-[3-(Pyridin-2-ylmethoxymethyl)-phenyl]-1H-benzoimidazol-5-yl}-methylamine;
N-{1-[3-(1-Methyl-1H-imidazol-2-ylmethoxymethyl)-phenyl]-1H-benzoimidazol-5-ylmethyl}-acetamide;
N-{1-[3-(Pyridin-2-ylmethoxymethyl)-phenyl]-1H-benzoimidazol-5-ylmethyl}-acetamide;
N-{1-[3-(2-Methyl-2H-[1,2,4]triazol-3-ylmethoxymethyl)-phenyl]-1H-benzoimidazol-5-ylmethyl}-acetamide;
N-{1-[3-(2-Methyl-2H-pyrazol-3-ylmethoxymethyl)-phenyl]-1H-benzoimidazole-5-ylmethyl}-acetamide;
N-{1-[3-(1,3-Thiazol-2-ylmethoxymethyl)-phenyl]-1H-benzoimidazole-5-ylmethyl}-acetamide;
1-[3-(2-Methyl-2H-[1,2,4]-triazol-3-ylmethoxymethyl)-phenyl]-5-trifluoromethyl-1H-benzoimidazole;
1-[3-(2-Ethyl-2H-[1,2,4]-triazol-3-ylmethoxymethyl)-phenyl]-5-trifluoromethyl-1H-benzoimidazole;
5-Methyl-1-[3-(2-methyl-2H-[1,2,4]triazol-3-ylmethoxymethyl)-phenyl]-1H-benzoimidazole;
1-{1-[3-(2-Methyl-2H-[1,2,4]triazol-3-ylmethoxymethyl)-phenyl]-1H-benzoimidazol-5-yl}-ethanone;
1-{1-[3-(2-Methyl-2H-[1,2,4]triazol-3-ylmethoxymethyl)-phenyl]-1H-benzoimidazol-5-yl}-ethanone oxime;
1-{1-[3-(2-Methyl-2H-[1,2,4]triazol-3-ylmethoxymethyl)-phenyl]-1H-benzoimidazol-5-yl}-ethanone O-ethyl-oxime;
1-{1-[3-(2-Methyl-2H-[1,2,4]triazol-3-ylmethoxymethyl)-phenyl]-1H-benzoimidazol-5-yl}-ethanone O-methyl-oxime;

1-{1-[3-(2-Methyl-2H-[1,2,4]triazol-3-ylmethoxymethyl)-phenyl]-1H-benzoimidazol-5-yl}-ethanol;
5-(1-Methoxy-ethyl)-1-[3-(2-methyl-2H-[1,2,4]triazol-3-ylmethoxymethyl)-phenyl]-1H-benzoimidazole;
5-(1-Ethoxy-ethyl)-1-[3-(2-methyl-2H-[1,2,4]triazol-3-ylmethoxymethyl)-phenyl]-1H-benzoimidazole;
5-Azidomethyl-1-[3-(thiazol-2-ylmethoxymethyl)-phenyl]-1H-benzoimidazole;
5-Azidomethyl-1-{3-(2-methyl-2H-[1,2,4]triazol-3-ylmethoxymethyl)-phenyl}-1H-benzoimidazole;
5-Azidomethyl-1-[3-(2-methyl-2H-pyrazol-3-ylmethoxymethyl)-phenyl]-1H-benzoimidazole;
C-{1-[3-(1,3-Thiazol-2-ylmethoxymethyl)-phenyl]-1H-benzoimidazole-5-yl}-methylamine;
C-{1-[3-(2-Methyl-2H-[1,2,4]triazol-3-ylmethoxymethyl)-phenyl]-1H-benzoimidazol-5-yl}-methylamine;
C-{1-[3-(2-Methyl-2H-pyrazol-3-ylmethoxymethyl)-phenyl]-1H-benzoimidazole-5-yl}-methylamine;
1-{3-[(3,4-Difluoro-benzylamino)-methyl]-phenyl}-1H-benzoimidazole-5-carboxylic acid ethyl ester;
1-(3-{[(Pyridin-2-ylmethyl)-amino]-methyl}-phenyl)-1H-benzoimidazole-5-carboxylic acid ethyl ester;
1-(3-{[(Pyridin-4-ylmethyl)-amino]-methyl}-phenyl)-1H-benzoimidazole-5-carboxylic acid ethyl ester;
1-(3-{[(Pyridin-3-ylmethyl)-amino]-methyl}-phenyl)-1H-benzoimidazole-5-carboxylic acid ethyl ester;
1-{3-[(3,4-Dichloro-benzylamino)-methyl]-phenyl}-1H-benzoimidazole-5-carboxylic acid ethyl ester;
(1-{3-[(3,4-Difluoro-benzylamino)-methyl]-phenyl}-1H-benzoimidazol-5-yl)-methanol;
(3,4-Difluoro-benzyl)-[3-(5-methoxymethyl-benzoimidazol-1-yl)-benzyl]-methyl-amine;
1-{3-[(3,4-Difluoro-benzylamino)-methyl]-phenyl}-1H-benzoimidazole-5-carbaldehyde;
1-{3-[(3,4-Difluoro-benzylamino)-methyl]-phenyl}-1H-benzoimidazole-5-carbaldehyde oxime;
or an N-oxide thereof, any of its isomers or any mixture of its isomers,
or a pharmaceutically acceptable salt thereof.

13. A pharmaceutical composition, comprising a therapeutically effective amount of a compound of claim 1, or an N-oxide thereof, any of its stereoisomers or any mixture of its stereoisomers, or a pharmaceutically acceptable salt thereof, together with at least one pharmaceutically acceptable carrier, excipient or diluent.

14. The compound of claim 12, wherein said compound is 5-(1-Ethoxy-ethyl)-1-[3-(2-methyl-2H-[1,2,4]triazol-3-ylmethoxymethyl)-phenyl]-1H-benzoimidazole or a pharmaceutically acceptable salt thereof.

15. The composition according to claim 13, wherein said compound is 5-(1-Ethoxy-ethyl)-1-[3-(2-methyl-2H-[1,2,4]triazol-3-ylmethoxymethyl)-phenyl]-1H-benzoimidazole or a pharmaceutically acceptable salt thereof.

\* \* \* \* \*